(12) United States Patent
Ismail et al.

(10) Patent No.: US 7,951,853 B2
(45) Date of Patent: *May 31, 2011

(54) POLYMER-BASED ANTIMICROBIAL AGENTS, METHODS OF MAKING SAID AGENTS, AND PRODUCTS INCORPORATING SAID AGENTS

(75) Inventors: Ashraf A. Ismail, Westmount (CA); Leonard Pinchuk, Miami, FL (US); Orley R. Pinchuk, Montreal West (CA); David Pinchuk, Montreal West (CA)

(73) Assignee: Smart Anti-Microbial Solutions, LLC, Stamford, CT (US)

( * ) Notice: Subject to any disclaimer, the term of this patent is extended or adjusted under 35 U.S.C. 154(b) by 1179 days.

This patent is subject to a terminal disclaimer.

(21) Appl. No.: 11/558,023

(22) Filed: Nov. 9, 2006

(65) Prior Publication Data

US 2007/0098806 A1     May 3, 2007

Related U.S. Application Data

(63) Continuation-in-part of application No. PCT/US2005/008360, filed on Mar. 11, 2005, which is a continuation-in-part of application No. 10/138,160, filed on May 2, 2002, now Pat. No. 6,905,711.

(51) Int. Cl.
*C08K 3/10* (2006.01)
*C08K 3/22* (2006.01)

(52) U.S. Cl. ........ 523/122; 424/422; 424/423; 424/443; 424/449; 424/486; 604/264; 604/265; 604/905

(58) Field of Classification Search .................. 424/405, 424/422–423, 443, 486; 514/413, 434; 523/122, 523/403
See application file for complete search history.

(56) References Cited

U.S. PATENT DOCUMENTS

| | | | | |
|---|---|---|---|---|
| 4,933,178 | A * | 6/1990 | Capelli | 424/403 |
| 5,945,032 | A | 8/1999 | Breitenbach et al. | |
| 6,306,419 | B1 * | 10/2001 | Vachon et al. | 424/422 |
| 6,379,712 | B1 | 4/2002 | Yan et al. | |
| 6,716,895 | B1 * | 4/2004 | Terry | 523/122 |
| 6,719,987 | B2 * | 4/2004 | Burell et al. | 424/405 |
| 6,827,874 | B2 | 12/2004 | Souter et al. | |
| 6,905,711 | B1 | 6/2005 | Tullo et al. | |
| 6,924,325 | B2 | 8/2005 | Qian | |
| 6,949,598 | B2 | 9/2005 | Terry | |
| 6,979,491 | B2 | 12/2005 | Yan et al. | |
| 2002/0051823 | A1 | 5/2002 | Yan et al. | |
| 2003/0091767 | A1 | 5/2003 | Podhajny | |
| 2003/0185889 | A1 | 10/2003 | Yan et al. | |
| 2004/0010215 | A1 | 1/2004 | Gibbens et al. | |
| 2005/0124724 | A1 | 6/2005 | Burton et al. | |
| 2005/0152992 | A1 | 7/2005 | Johnson, Jr. et al. | |
| 2005/0214246 | A1 * | 9/2005 | Mhaskar et al. | 424/78.1 |
| 2005/0266981 | A1 | 12/2005 | Nakajima et al. | |
| 2006/0018967 | A1 | 1/2006 | Schildhauer | |
| 2006/0147549 | A1 | 7/2006 | Grab et al. | |
| 2007/0084308 | A1 * | 4/2007 | Nakamura et al. | 75/346 |

FOREIGN PATENT DOCUMENTS

WO     WO2006098729 A1     9/2006

OTHER PUBLICATIONS

"Nano Silver" downloaded from internet on Jun. 5, 2006, www.nano-silver.com.
Serendipity Laboratories High Voltage Colloidal Silver, first downloaded from internet on Jun. 20, 2006, www.colloidalsilver.biz/faq.html.
Kevin Bouffard "A New Tactic to Battle Canker: Call in the Coppers (Spray, That is)" The Ledger Online, Published Feb. 5, 2006, www.theledger.com/apps/pbcs.dll/article?AID=/20060205/NEWS/602050436.
Kearney Plant Protection Group Newsletter, Cooperative Extension, Plant Protection Quarterly, Jan. 1997, vol. 7, No. 1.
Kearney Plant Protection Group Newsletter, Cooperative Extension, Universtiy of California, Plant Protection Quarterly, Jan./Apr. 1993, vol. 3, Nos. 1 & 2.

* cited by examiner

*Primary Examiner* — Michael G Hartley
*Assistant Examiner* — Jagadishwar R Samala
(74) *Attorney, Agent, or Firm* — Gordon & Jacobson, PC

(57) ABSTRACT

The present invention relates to antimicrobial agents, methods for the production of these agents, and the use of these agents. The antimicrobial agent of the present invention includes a water-soluble polymer and oligodynamic metal ions which interact with counter-ions of the polymer such that the metal ions are bound to corresponding counter-ions. The water-soluble polymer controls a sustained release of the metal ions. The oligodynamic metal ions preferably include small size metal particles (e.g., nano-sized silver particles) that interact to the water-soluble polymer as well as metal ions derived from one or more water-soluble oligodynamic metal compositions (e.g., metal sulfates and/or metal nitrates). The agent may also include one or more acids, including organic acids (such as sulfates, carboxylic acids, amines, hydroxyls, nitrates, and phosphates) and/or non-organic acids (such as boric acid and dioctylborate).

20 Claims, No Drawings

POLYMER-BASED ANTIMICROBIAL AGENTS, METHODS OF MAKING SAID AGENTS, AND PRODUCTS INCORPORATING SAID AGENTS

CROSS-REFERENCE TO RELATED APPLICATIONS

This application is a continuation-in-part of PCT App. No. PCT/US05/08360, filed on Mar. 11, 2005, which is a continuation-in-part of U.S. application Ser. No. 10/138,160, filed on May 2, 2002, and issued on Jun. 14, 2005, as U.S. Pat. No. 6,905,711, both of which are hereby incorporated herein by reference in their entireties.

BACKGROUND OF THE INVENTION

1. Field of the Invention

The invention relates to antimicrobial agents, products incorporating such agents, and methods of making such products. More particularly, the invention relates to polymer-based antimicrobial agents.

2. State of the Art

Silver and silver salts are commonly used as antimicrobial agents. An early medicinal use of silver was the application of aqueous silver nitrate solutions to prevent eye infection in newborn babies. Silver salts, colloids, and complexes have also been used to prevent and to control infection. Other metals, such as gold, zinc, copper, and cerium, have also been found to possess antimicrobial properties, both alone and in combination with silver. These and other metals have been shown to provide antimicrobial behavior even in minute quantities, a property referred to as "oligodynamic."

Metallic antimicrobials function by releasing metal ions into the microbe. The released ions react with protein and other anions (negative charged species) in the microbe and render the protein insoluble and thereby inactive. The inactive protein perturbs cellular function, disrupts membranes and prevents the normal activity and reproduction of DNA thereby essentially killing the microorganism.

U.S. Pat. No. 6,306,419 to Vachon et al. discloses a polymer-based coating comprising a styrene sulfonate polymer with a carrier molecule bound to silver ion incorporated therein. The styrene sulfonate polymer is prepared by reacting an acetyl sulfate sulfonation agent with a styrene copolymer in 1,2-dichloroethane (DCE). The coating is hydrophilic such that it retains a relatively large amount of water or water-containing fluid. There are several disadvantages to this composition. One such disadvantage is that larger quantities of the silver metal are required to provide effective antimicrobial activity. A second disadvantage is that the carrier molecule is required which renders it more expensive as well as more difficult to dispose of the carrier byproduct. A third disadvantage is that a solvent other than water (e.g. DCE) is required to prepare the polymer matrix. Such solvents are typically hazardous because of their reactive nature and thus require special care in handling and disposing of such solvents, which limits the widespread acceptance of such antimicrobial polymers in many applications.

SUMMARY OF THE INVENTION

It is therefore an object of the invention to provide a polymer-based antimicrobial agent that is readily soluble in a water solution.

It is also an object of the invention to provide such a polymer-based antimicrobial agent that does not require relatively large quantities of the metal in order to provide effective antimicrobial activity.

It is another object of the invention to provide methods of incorporating such an antimicrobial agent as part of a product or service, such as a paper product, for mold abatement in residential and/or commercial applications, or for treating and/or preventing citrus canker.

In accord with these objects, which will be discussed in detail below, the antimicrobial agent of the present invention includes a water-soluble polymer and oligodynamic metal ions which interact with counter-ions of the polymer such that the metal ions are bound to corresponding counter-ions. The water-soluble polymer controls a sustained release of the metal ions. The oligodynamic metal ions preferably include small size metal particles (e.g., nano-sized silver particles) that ionically bond or are electrostatically bound to the water-soluble polymer as well as metal ions derived from one or more water-soluble oligodynamic metal compositions (e.g., metal sulfates and/or metal nitrates). The small-size particles can aid in reducing the photosensitivity of the agent, and thus counter the proclivity of the agent to change color when subjected to light. The agent may also include one or more acids, including organic acids (such as sulfates, carboxylic acids, amines, hydroxyls, nitrates, and phosphates) and/or non-organic acids (such as boric acid and dioctylborate). This allows the total concentration of oligodynamic metal in the agent to be reduced significantly while maintaining or even enhancing antimicrobial activity.

Additional objects and advantages of the invention will become apparent to those skilled in the art upon reference to the detailed description.

DETAILED DESCRIPTION OF THE PREFERRED EMBODIMENTS

The following definitions are used in the description below. The terms "colloid" and "colloidal" refer to a solution consisting of particles suspended in a liquid medium. An "ion" is an atom or a group of atoms that has acquired a net electric charge. The term "ionic" refers to a condition where an ion has an electric charge. An "electrostatic charge" is a charge that can be induced in a substance, for example, metallic silver particles, by passing a current over the substance. An "electrostatic attraction" is when a substance or particle with an electrostatic charge is attracted to a second substance which contains the opposite charge to the substance. "Water-soluble" means that the composition has a solubility of at least 2 g in 100 g of water at room temperature. "Small size" in reference to metal particles means metal particles that have a size less than 1 μm in diameter and more preferably less than 0.01 μm in diameter. "Nano-size" or "Nano" in reference to metal particles means metal particles that have a size between 1 nm and 100 nm in diameter.

According to the invention, an antimicrobial agent is realized from a water-soluble polymeric substance that has pendant hydrophilic groups that are capable of binding with one or more oligodynamic metal ions. Preferably, the hydrophilic groups of the polymer are capable of binding with one or more positively charged oligodynamic metal ions. Therefore, it is preferred that the water-soluble polymeric substance have negatively charged hydrophilic groups such as sulfates, phosphates, nitrates, carboxylates and the like. The water-soluble polymeric substance is dissolved in an aqueous solution. The aqueous solution preferably comprises water without any alcohols or other organic solvents. However, the aqueous solution can include one or more alcohols or other organic solvents (e.g., m-pyrol, dimethylformamide, dimethylacetamide, dimethyl sulfonamide, tetrahydrofuran, mixtures of the above, mixtures of the above with swelling solvents such as diethyl ether, xylene, toluene and the like) preferably in a range between 5% and 50% by weight. One or more compositions that include an oligodynamic metal are added to the polymeric aqueous solution. The oligodynamic metal(s) can be a noble metal (such as Ag, Au, Pt, Pd, Ir) or a heavy metal (such as Cu Sn, Sb, Bi and Zn). Preferably, the one or more oligodynamic metal compositions include small size metal particles (most preferably, nano-sized silver particles) that carry an electrostatic charge and that dissolve or disperse in the polymeric aqueous solution and ionically bond to the hydrophilic group of the polymer. Such small size metal particles can also remain suspended as a colloid in the polymeric aqueous solution wherein the electrostatic charge carried by the small size metal particles can maintain the particles within the polymer matrix (in contrast to residing solely in solution) by electrostatic attraction. The one or more oligodynamic metal compositions added to the polymeric aqueous solution also preferably include at least one water-soluble metal composition of an oligodynamic metal that dissolves in the polymeric aqueous solution and ionically bonds to the hydrophilic group of the polymer. One or more acids (e.g., organic acids and inorganic acids) can be added to the mixture.

The range of total solids dissolved in water can be from 0.1% to 5%, preferably from 0.3% to 3% and more preferentially 0.5 to 2.5%. Looking now only at the solid components without water, the range of small-size metal particles (e.g., nano-sized silver particles) is preferably from 0.05 to 5% and most preferably from 0.5 to 3%; the range of water soluble polymer is preferably from 1 to 20%, and most preferably from 5 to 6%; and the range of other oligodynamic metal compositions preferably in a range from 10 to 25%. The remaining solid content includes acids, organic and inorganic, that can comprise 50% to 75%, and most preferably from 70 to 75% of the solids component. This combination of reagents allows the total concentration of oligodynamic metal in the polymeric aqueous solution to be reduced significantly while maintaining or even enhancing antimicrobial activity.

Examples of hydrophilic polymers which may be used to form the compositions include, but are not limited to, polyurethanes, including sulfonated polyether polyurethanes, sulfonated polyester polyurethanes, sulfonated polyurethaneureas, and their copolymers, especially the polyethleneoxide copolymers; polyvinylpyrrolidones; polyvinyl alcohols; polyethylene glycols and their copolymers; polypropylene glycols and their copolymers; polyoxyethylenes and their copolymers; polyacrylic acid; polyacrylamide; carboxymethyl cellulose; cellulose and its derivatives; dextrans and other polysaccharides; starches; guar; xantham and other gums and thickeners; collagen; gelatins; and other biological polymers. All the of these hydrophilic polymers can be reacted or co-polymerized with charged moieties to render them both water soluble as well as ionically charged. Examples of these charged moieties include, sulfonation of the aromatic rings on aromatic polyurethanes; addition of methacrylic acid in the vinyl-based polymers. Also included are normally hydrophobic polymers that are rendered both hydrophilic and anionic by the addition of functional groups; for example, polystyrene is hydrophobic but can be rendered water soluble by sulfonating the styrene group. Similarly, polyethylene terepthalate (PET) can be rendered hydrophilic and anionic by sulfonating the terepthalic groups. The preferred polymer is water soluble polystyrene with its copolymers, such as sulfonated polystyrene co-maleic acid.

The antimicrobial agent of the invention is illustrated in the following example. A water-soluble sulfonated polystyrene is dissolved in water. Nano-size silver particles are added to the sulfonated polystyrene water solution and mixed together. The silver particles carry a positive electrostatic charge and dissolve or disperse in the polymeric aqueous solution and interact with the sulfonated polystyrene by ionic bonding wherein the sulfonate groups of the sulfonated polystyrene are the counter-ions to positively-charged silver ions. In this manner, the polymer controls a sustained release of the positively-charged silver ions. The silver particles can also remain suspended as a colloid in the polymeric aqueous solution wherein the positive electrostatic charge carried by the silver particles can maintain the silver particles within the sulfonated polystyrene matrix (in contrast to residing solely in solution) by electrostatic attraction. In this case, the positively electrostatically charged nano-sized silver particles are attracted to the polar sulfonate groups of the sulfonated polystyrene. Advantageously, the nano-size silver particles aid in reducing the photosensitivity of the resulting composition, and thus counter the proclivity of the antimicrobial agent to change color when subjected to light. It is therefore desirous that when nano-sized silver particles are used, the silver ion-bound silver is reduced accordingly. In other words, if more nano-sized silver particles with electrostatic charge is used, then other silver moieties such as colloidal silver salts or silver ion, from, for example, silver nitrate or silver sulfate can be reduced in quantity.

Other water-soluble metal compositions that include an oligodynamic metal (or solutions based thereon) are added to the silver/sulfonated polystyrene water mixture and mixed together. Preferably, such water-soluble metal compositions include metal sulfates (such as copper (II) sulfate or zinc sulfate) and/or metal nitrates (such as silver nitrate, copper (II) nitrate and/or zinc nitrate). The ions of the oligodynamic metal composition(s) react with counter-ions of the polymer such that the metal ions are ionically bound to corresponding counter-ions, and the polymer controls a sustained release of the metal ions.

One or more organic acids can be added to the oligodynamic metal/sulfonated polystyrene/water mixture and mixed together. This allows the total concentration of oligodynamic metal in the mixture to be reduced significantly while maintaining or even enhancing antimicrobial activity. Examples of organic acids include citric acid, malic acid, ascorbic acid, salicyclic acid, acetic acid, formic acid and the like. In addition to the organic acids, other mildly acidic acids can also be used in this cocktail such as boric acid, dioctylborate, and the like.

Table 1 shows various concentrations of colloidal silver, metal compositions and acids that are mixed and reacted to a water-soluble sulfonated polymer carrier (showing actual amounts used and percentages).

| Chemical | Grams | Percent (Wt/Wt) including water | Percent (Wt/Wt) without water |
|---|---|---|---|
| nano-sized silver | 0.050 | 0.005 | 2.444 |
| sulfonated polystyrene | 0.120 | 0.012 | 5.865 |

-continued

| Chemical | Grams | Percent (Wt/Wt) including water | Percent (Wt/Wt) without water |
|---|---|---|---|
| copper (II) sulfate | 0.203 | 0.020 | 9.922 |
| zinc sulfate | 0.203 | 0.020 | 9.922 |
| boric acid | 0.490 | 0.049 | 23.949 |
| malic acid | 0.490 | 0.049 | 23.949 |
| citric acid | 0.490 | 0.049 | 23.949 |
| water | 1000 | 99.796 | |
| Total | 1002.046 | 100 | 100 |

The specific example of Table 1 employs divalent metals; however, monovalent or multivalent metals can also be used. Also note that when the organic carboxylic acids shown are mixed with the sulfonated polymer and the oligodynamic metal composition, a competing reaction occurs where some portion of the metal will couple with the sulfonated polymer and another portion of the metal will couple with the organic carboxylic acid(s). In the case where the metal couples with the sulfonated polymer, the counter ion is the sulfonate group on the polymer. In the case where the metal couples with the organic carboxylic acid(s), the counter ion is the organic carboxylic acid. The result of this competing reaction will depend on the stoichiometry, relative affinity and strength of the ionic bond.

The liquid mixture of materials described above can be dried and ground to a fine powder and commercialized as a powdered-form antimicrobial agent. In this case, the solid content of the powdered-form antimicrobial agent preferably includes the following:

small-size metal particles (e.g., nano-sized silver particles) in a range preferably from 0.05 to 5% and most preferably from 1 to 3%;

water soluble polymer in a range preferably from 1 to 20%, and most preferably from 5 to 7%;

acids in a range preferably from 10 to 75%, and most preferably from 70 to 75%; and other oligodynamic metals in a range preferably from 5 to 25%.

With such product, the user need only dilute the powder in an aqueous solution (which preferably includes only water but can include other solvents) to the desired concentration and spray, dip or drop the solution onto the substance to be coated. The powder may also be diluted in a water solution (or solvent solution) and added as part of an admixture during formation of the end product. For example, the admixture may be a pulp that is processed to form a paper product. Here the solids content can range from 0.001 to 10%; preferably 0.1 to 2% of the solution used to coat the product. When the water evaporates, a thin film of polymer remains on the substrate where the thin polymer film binds the anti-microbial agents. In such applications, the ions of the oligodynamic metal compositions therein interact with counter-ions of the water-soluble polymer such that the metal ions are bound to corresponding counter-ions and the polymer controls a sustained release of the metal ions.

The powdered-form antimicrobial agent of the present invention has many potential applications, including the abatement of mold in residential and commercial applications as well as for treatment and prevention of citrus canker in citrus groves. When used for mold abatement, the powdered-form antimicrobial agent as described above is dissolved in an aqueous solution, which is applied in spray form onto wallboard, walls, floors, ceilings, or other home/building structural members. When used for treatment and prevention of citrus canker, the powdered-form antimicrobial agent as described above is dissolved in an aqueous solution, which is applied in spray form onto the leaves and/or branches and/or trunk of the citrus tree. For citrus canker applications, the solids concentrations of the powdered-form antimicrobial agent in the spraying mixture can range from 0.001 to 10%, and preferably from 0.1 to 2%. It is preferable that the mixture also contain a tackifier to help stick the antimicrobial mixture to the leaves and/or branches and/or trunk of the tree. An exemplary tackifier for this application includes one or more water soluble substances that are sticky; such as syrup (maple, corn, etc.), tree sap, polysaccharides, honey, vegetable oil derivatives and the like. The concentration of tackifier may comprise 0.1 to 2% of the diluted formulation. In addition, the viscosity of the solution may be increased, which will help suspend the additives in aqueous solution to help in spraying applications of the system. Thickening can be accomplished by adding more water soluble polymer or thickeners such as gums (agar, xanthum, guar, gellan, pectin), polysaccharide, gelatin, corn starch, and the like. The amount of thickener can range from 0.2 to 2%, with 0.5% of the total bath weight.

There have been described and illustrated herein antimicrobial agents, products incorporating said agents and methods of making the antimicrobial agents and products incorporating them. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. An antimicrobial agent comprising:
   a water-soluble hydrophilic polymer component having a sulfonate group; and
   a plurality of oligodynamic metal compositions that include small-size particles of silver, a composition of copper, and a composition of zinc;
   wherein total weight of said plurality of oligodynamic metal compositions is at least 3.5 times the total weight of said water-soluble hydrophilic polymer component; and wherein said water-soluble hydrophilic polymer component comprises a polymer selected from the group consisting of sulfonated polyurethane and sulfonated polystyrene.

2. An antimicrobial agent according to claim 1, wherein: the small-size particles of silver include nano-size particle.

3. An antimicrobial agent according to claim 1, further comprising:
   at least one acid.

4. An antimicrobial agent according to claim 3, wherein: the at least one acid is 10 to 75% of the solid content of the agent.

5. An antimicrobial agent according to claim 3, wherein: the at least one acid comprises at least organic acid.

6. An antimicrobial agent according to claim 5, wherein: the at least one organic acid is selected from the group including acetic acid, citric acid, malic acid, ascorbic acid, salicyclic acid, and formic acid.

7. An antimicrobial agent according to claim 3, wherein: the at least one acid comprises at least one non-organic acid.

8. An antimicrobial agent according to claim 7, wherein:
the at least one non-organic acid is selected from the group including boric acid and dioctylborate.

9. An antimicrobial agent according to claim 1, wherein:
the silver particles are 0.05 to 5% by weight of solid content of the agent.

10. An antimicrobial agent according to claim 1, wherein:
the silver particles have a diameter between 1 nm and 100 nm.

11. An antimicrobial agent according to claim 1, wherein:
the compositions of copper and zinc are 5 to 25% by weight of the solid content of the agent.

12. An antimicrobial agent according to claim 1, wherein:
the composition of copper comprises copper (II) sulfate, and the composition of zinc comprises zinc sulfate.

13. An antimicrobial agent according to claim 1, wherein:
the composition of copper comprises copper (II) nitrate, and the composition of zinc comprises zinc nitrate.

14. An antimicrobial agent according to claim 1, further comprising a polymer component selected from the group consisting
of carboxylic acids, amines, hydroxyls, nitrates, and phosphates.

15. An antimicrobial agent according to claim 1, wherein:
the water-soluble hydrophilic polymer component is 5 to 7% by weight of the solid content of the agent.

16. An antimicrobial agent according to claim 1, wherein:
said water-soluble hydrophilic polymer component and said plurality of oligodynamic metal compositions are diluted in an aqueous solution.

17. An antimicrobial agent according to claim 16, further comprising:
a tactifier that is added to the aqueous solution.

18. An antimicrobial agent according to claim 17, wherein:
the tactifier comprises at least one water soluble substance selected from the group including syrup, tree sap, polysaccharides, honey, vegetable oil derivatives.

19. An antimicrobial agent according to claim 1, wherein:
the agent has a solid powder-form suitable for dissolving in an aqueous solution for application thereof.

20. An antimicrobial agent according to claim 1, wherein:
total weight of the small-size particles of silver is at least 10% of the total weight of said plurality of oligodynamic metals compositions.

* * * * *